United States Patent
Herrmann et al.

(10) Patent No.: US 10,585,046 B2
(45) Date of Patent: *Mar. 10, 2020

(54) APPARATUS AND METHOD FOR TRACKING DEFECTS IN SHEET MATERIALS

(71) Applicants: Jürgen-Peter Herrmann, Rosenheim (DE); Marius Michael Herrmann, Rosenheim (DE); Wolfgang Schorn, Hönningen (DE)

(72) Inventors: Jürgen-Peter Herrmann, Rosenheim (DE); Marius Michael Herrmann, Rosenheim (DE); Wolfgang Schorn, Hönningen (DE)

(73) Assignee: KHS GmbH, Dortmund (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/446,127

(22) Filed: Jun. 19, 2019

(65) Prior Publication Data

US 2019/0302032 A1  Oct. 3, 2019

Related U.S. Application Data

(60) Division of application No. 15/016,415, filed on Feb. 5, 2016, now Pat. No. 10,365,228, which is a (Continued)

(30) Foreign Application Priority Data

Aug. 6, 2013 (DE) .................. 10 2013 108 485

(51) Int. Cl.
*G01N 21/88* (2006.01)
*G01N 21/86* (2006.01)
(Continued)

(52) U.S. Cl.
CPC ......... *G01N 21/8851* (2013.01); *B65H 26/02* (2013.01); *B65H 26/066* (2013.01);
(Continued)

(58) Field of Classification Search
CPC .. G01N 21/8851; G01N 21/86; G01N 21/958; G01N 2021/888;
(Continued)

(56) References Cited

U.S. PATENT DOCUMENTS 3,760,667 A 9/1973 Maxey
4,073,260 A 2/1978 Bosworth
(Continued)

FOREIGN PATENT DOCUMENTS

CN 101393141 A 3/2009
CN 101035946 B 3/2011
(Continued)

OTHER PUBLICATIONS

"Laser Surface Authentication™: Natural Randomness as a Fingerprint for Product Authentication and Tracking", © Ingenia Technology (UK) Ltd, 2010.
(Continued)

*Primary Examiner* — Sang H Nguyen
(74) *Attorney, Agent, or Firm* — Nils H. Ljungman & Associates (57) ABSTRACT

An apparatus and method for tracking defects in sheet materials. The abstract of the disclosure is submitted herewith as required by 37 C.F.R. § 1.72(b). As stated in 37 C.F.R. § 1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and
(Continued)

gist of the technical disclosure. The abstract shall not be used for interpreting the scope of the claims. Therefore, any statements made relating to the abstract are not intended to limit the claims in any manner and should not be interpreted as limiting the claims in any manner.

20 Claims, 2 Drawing Sheets

Related U.S. Application Data continuation-in-part of application No. PCT/EP2014/066630, filed on Aug. 1, 2014.

(51) Int. Cl.
*G01N 21/958* (2006.01)
*B65H 26/02* (2006.01)
*B65H 26/06* (2006.01)

(52) U.S. Cl.
CPC ........... *G01N 21/86* (2013.01); *G01N 21/958* (2013.01); *B65H 2511/512* (2013.01); *B65H 2511/52* (2013.01); *B65H 2553/42* (2013.01); *B65H 2553/45* (2013.01); *B65H 2557/51* (2013.01); *B65H 2557/62* (2013.01); *B65H 2557/64* (2013.01); *B65H 2701/12* (2013.01); *B65H 2701/173* (2013.01); *G01N 2021/8663* (2013.01); *G01N 2021/888* (2013.01); *G01N 2201/06113* (2013.01)

(58) Field of Classification Search
CPC . G01N 2021/8663; G01N 2201/06113; B65H 26/066; B65H 26/02; B65H 2511/512; B65H 2511/52; B65H 2553/42; B65H 2553/45; B65H 2557/62; B65H 2557/64; B65H 2701/12; B65H 2701/173
See application file for complete search history.

(56) References Cited

U.S. PATENT DOCUMENTS

| | | | | |
|---|---|---|---|---|
| 4,746,020 A * | 5/1988 | Schenk | ................ | G01N 21/894 101/219 |
| 4,934,228 A * | 6/1990 | Bolton | .................... | B07C 5/361 118/37 |
| 5,115,144 A | 5/1992 | Konishi | | |
| 5,642,198 A | 6/1997 | Long | | |
| 5,767,975 A | 6/1998 | Ahlen | | |
| 6,333,987 B1 * | 12/2001 | Reinhard | ............ | B41F 33/0036 382/100 |
| 6,369,882 B1 * | 4/2002 | Bruner | .................... | B07C 5/342 209/577 |
| 6,717,168 B2 * | 4/2004 | Eisen | ................. | B65H 23/0216 250/559.36 |
| 7,218,386 B2 * | 5/2007 | Alcock | ................. | G01N 21/474 356/71 |
| 7,369,240 B1 * | 5/2008 | Abbott | ................. | G01N 21/896 356/429 |
| 7,397,746 B2 * | 7/2008 | Jung | ..................... | G11B 19/124 369/53.22 |
| 8,411,276 B2 * | 4/2013 | Doak | ...................... | B07C 5/342 356/445 |
| 8,755,121 B2 | 6/2014 | Cape et al. | | |
| 8,786,839 B2 | 7/2014 | Cronin et al. | | |
| 8,867,134 B2 | 10/2014 | Steenblik et al. | | |
| 9,050,735 B2 * | 6/2015 | LaCroix | ............... | B23D 45/042 |
| 9,220,446 B2 | 12/2015 | Cronin et al. | | |
| 9,835,552 B2 | 12/2017 | Wagner | | |
| 2002/0154308 A1 | 10/2002 | Uesugi | | |
| 2004/0051059 A1 | 3/2004 | Ungpiyakul | | |
| 2007/0165208 A1 | 7/2007 | Cowburn et al. | | |
| 2008/0062422 A1 * | 3/2008 | Thomas | ............... | G01N 21/896 356/432 |
| 2009/0088889 A1 | 4/2009 | Hellstrom et al. | | |
| 2009/0283583 A1 | 11/2009 | Cowburn et al. | | |
| 2010/0007930 A1 | 1/2010 | Cowburn | | |
| 2010/0063750 A1 | 3/2010 | Floeder | | |
| 2010/0316251 A1 | 12/2010 | Cowburn et al. | | |
| 2011/0211895 A1 | 9/2011 | Inaba | | |
| 2012/0057162 A1 | 3/2012 | Burkatovsky | | |
| 2013/0083324 A1 | 4/2013 | Wilhelm | | |

FOREIGN PATENT DOCUMENTS

| | | |
|---|---|---|
| DE | 10 2004 010 479 A1 | 10/2005 |
| DE | 10 2009 029 084 A1 | 3/2011 |
| EP | 2 110 776 A2 | 10/2009 |
| GB | 919664 | 2/1963 |
| JP | H0450704 | 2/1992 |
| JP | 09109372 | 4/1997 |
| JP | 2000241358 | 9/2000 |
| JP | 2013134136 | 7/2013 |

OTHER PUBLICATIONS

"Laser Surface Authentication™: Natural Randomness as a Fingerprint for Product Authentication" by Mark McGlade, Director Business Development, Ingenia Technology Ltd., © Ingenia Technology (UK) Ltd, 2006.

"Laser-Streulichtmessungen zur Verpackungsidentifizierung und -verfolgung: Einsatzmöglichkeiten in der Prozessindustrie" by Ludger Brüll and Martin Friedrich, Bayer Technology Services GmbH, 2007.

"PROTEXXION Powered by LSA: Die neue Dimension der Fälschungssicherheit: Eindeutige Authentifizierung ohne Markierung", © Bayer Technology Services, 2007.

* cited by examiner

APPARATUS AND METHOD FOR TRACKING DEFECTS IN SHEET MATERIALS

CONTINUING APPLICATION DATA

This application is a Continuation-In-Part application of International Patent Application No. PCT/EP2014/066630, filed on Aug. 1, 2014, which claims priority from Federal Republic of Germany Patent Application No. 10 2013 108 485.0, filed on Aug. 6, 2013. International Patent Application No. PCT/EP2014/066630 was pending as of the filing date of this application. The United States was an elected state in International Patent Application No. PCT/EP2014/066630.

BACKGROUND

1. Technical Field

The present application relates to an apparatus and method for tracking defects in sheet materials.

2. Background Information

Background information is for informational purposes only and does not necessarily admit that subsequently mentioned information and publications are prior art.

The present application relates to a method and an apparatus for marking a material defect in a sheet material.

During the processing of sheet materials, such as, for example, metal sheets, paper sheets, or also plastic films, the sheet materials are unrolled, then guided through the respective processing stations, and then rolled up again or, for example, divided into sections.

During guiding through the processing stations, the sheet material is examined for material defects. For example, an optical examination may be carried out on the sheet material, and then any defective points can be marked for identification. For identification, for example, color markings can be applied, or a marking substance or marker can be introduced into the sheet material.

The processing of the material defect usually takes place after the running through the processing stations or, if appropriate, in a separate work stage, in which the sheet material is again unrolled. In any event, the sheet material runs through numerous stations of the apparatus between the detection of the defect and the processing of the defect, such as, for example, deflection rolling. As a result of this, the markings which have been applied, which identify the material defect, are frequently altered or removed, such that the position of the material defect cannot be determined with certainty.

In order to be able to locate the material defect despite defective identification marking, it is possible, as an alternative, to determine the run-through speed of the sheet material through the processing stations, such that, by way of a calculation, the position of the material defect can be determined or calculated. In other words, the speed at which the material is run through the system can be utilized to calculate when the portion of the sheet material containing the defect would be expected to pass or go through a certain point or area in the processing stations downstream of the defect-detection region.

Such calculation systems, however, are extremely imprecise, and with sheet materials, which, for example, are stretched or shrunk during the processing, are highly unreliable, such that reliable location of the material defect cannot be effected, or, for the processing of the material defects, it may be necessary and/or desired for substantially larger sheet sections to be processed. In other words, there are different factors that can make it difficult to reliably and consistently determine, by calculation, the expected location of the material defect downstream in processing. One factor is the general imprecision of most calculation systems. Another factor can be the sheet material itself. Some sheet materials, such as plastic film, may stretch or shrink during processing or handling of the sheet material. These different factors can affect the precision and/or accuracy of the detection and handling process.

For example, a defect-detection station or mechanism or unit could be used to inspect sheet material passing thereby or therethrough, and thus detect an area or a portion or a section of the sheet material that contains a material defect. In order to treat or process the material defect, a defect-processing station or mechanism or unit is positioned downstream of the defect-detection station. A calculation could then be performed, based on the speed of movement or travel of the sheet material through the overall sheet-handling machine, to determine or calculate or estimate when the portion of the sheet material containing the material defect will be passing by or through the defect-processing station. Using the known lengthening or stretching and speed characteristics of the sheet material related to the process which the sheet is undergoing, the computer system can approximate when and where the defect will arrive at the downstream sensing location. The processing is thus performed in essentially a "blind" manner based strictly on the calculation. In other words, a section of sheet material can be processed based on the calculation and expectation that the defect detected upstream will be in the section of sheet material in the defect-processing station at the calculated time, and not whether or not the defect is actually present in the section of sheet material being processed. Thus, if the calculation is erroneous or sufficiently imprecise, as can often be the case with many calculation systems, the defect-processing station will process a section of material that does not contain a defect, which is undesirable. Not only will sheet material of acceptable quality be processed, such as by removal, but the defect will remain in the sheet material that proceeds on for further use. Obviously, such waste of acceptable material and failure to process defective material is undesirable. In addition, if the material is generally prone to stretching or shrinking during handling, the section of the sheet material containing the defect will either arrive earlier or later at the defect-processing station than would be expected by the calculation. As a result of the imprecision of calculation and/or variability in the characteristics of the sheet material, larger amounts of material often must be processed in order to compensate for the imprecision, which can be wasteful. Thus, if no markings are available to mark exactly where a defect is in the sheet material, the user must choose either between a very imprecise detection, or a wasteful compensation process, neither of which are desirable.

As discussed above, the sheet material to be processed or handled could be different materials, such as paper, cellulose, plastic, metal, a metallic material, or other materials suitable for commercial use, such as in the container manufacturing industry or product packaging industry. The material defects could be such things as cracks, micro-cracks, tears, rips, bubbles, distortions, warping, discoloration, marks, misprints, folds, creases, wrinkles, holes, perforations, depressions, recesses, thinned portions, thickened portions, oil spots, or any other defect that would or could have a negative effect on the structural quality or aesthetic quality of the sheet material.

OBJECT OR OBJECTS

The present application is therefore based on an object of providing a method and an apparatus with which a material defect in a sheet material can be marked for identification precisely or substantially precisely, reliably or substantially reliably, and permanently or substantially permanently.

SUMMARY

The present application solves this object by a method for the marking of a material defect in a sheet material according to the present application and with an apparatus with the features disclosed in the present application. Further embodiments of the present application are presented in the present application.

The method of the present application for the marking of a material defect in a sheet material comprises at least the following steps:
  Detection of a material defect in a moving sheet material by a defect sensor,
  Detection of a surface structure feature in the region of the material defect detected by a first marking sensor and ascertaining of a first structure data record representing the surface structure feature, and
  Storing the structure data record in a storage device.

The method and apparatus according to the present application are based on the recognition that each surface of an object exhibits individually unique structure features, which can be used for the identification of an object. Even with close to identical objects, the surface structures differ in such a way that an unambiguous identification of the respective object is possible. A structure feature detected in a surface section therefore represents an unambiguous "fingerprint" for repeat recognition.

With regard to the detection of such an individual structure feature of the surface in the region of the material defect, the position at which the material defect is located in the sheet is to be determined exactly or substantially exactly or generally. In order to find the material defect again at a later point in time, the sheet material can be searched with the aim of finding the surface structure feature which was detected. Once the surface structure feature has been found again, the position of the material defect will therefore also be found. As a result, the identification markings which were conventionally used previously, introduced onto or into the sheet material, can be done away with. In other words, the system, according to at least one possible embodiment, utilizes the inherent structural features or characteristics of the sheet material itself as a "marking" of sorts to identify the section of the sheet material containing the defect.

Because the method of the present application is also well-suited for detecting a plurality of material defects and surface structure features in a sheet material, without stopping or slowing down the sheet material, the method of the present application can additionally be carried out in an economical manner.

The sheet material section which is to be examined in order to determine the surface structure feature can, in this situation, be independent of the region of the material defect, i.e., it is not necessary or it may not be desired for a section in the region of the material defect to be examined, but it should be at least in the immediate or substantially immediate vicinity. The region of the sheet material in which the surface structure feature is detected can be located, for example, in the plane of the material defect that is transverse to the direction of run of the sheet. The region to be examined can also be defined specifically or substantially specifically or generally with regard to a reference point of the sheet material, such as, for example, the outer edge, such that the detection of the surface structure feature takes place, for example, at a distance interval of twenty centimeters to the outer edge, and at the height of the material defects. In other words, the system can be used to detect portions or sections of the material sheet that contain the defect, or portions or sections that do not contain the defect. Portions or sections of the material sheet that do not contain or are not immediately adjacent to the defect can be used as reference points to determine the location of the defect. For example, the detected or noted portion or section of the material sheet could be a predetermined distance from the actual defect, and thus could be used to determine where the defect is located, even though the detected portion does not in itself contain the defect.

The detection of the material defect and the surface structure feature takes place while the sheet material is moving, i.e., during the detection, a relative change of position of the sheet material takes place in relation to the sensors.

The term "surface structure feature" is understood to mean one or more structures on or in the surface of an object. This may involve, in one possible embodiment, natural structures, i.e., structures which have come into being during the manufacture or processing of the object, and not introduced or applied subsequently or as additional structures to the surface. For example, one type of material might possibly have an inherent pattern or color arrangement in the material itself that could be used to identify sections of the material.

In order to obtain particularly or relatively simple access to the stored structure data record, the memory unit is formed as an external memory, to which access can be made, for example, by means of a control device and further devices for the processing of the sheet material.

The term "structure data record" is understood to mean a data record which represents the surface feature which has been detected, in one possible embodiment in the form of numerical values. Depending on the means of function of the marking sensor, this can be, for example, a converted picture file. It should be noted that the "marking sensor" does not actually place a mark or marker on or in the sheet material itself, but rather notes or "marks" the detected section or portion of the sheet material in the data records or files. Thus, discussion of a mark or marking of the sheet material, according to at least one possible embodiment, refers to a digital or electronic marking or mark or note in the data records.

According to a further embodiment of the present application, after the steps for the marking of the sheet material according to the present application, the surface structure feature for the detection and processing of the material defect is acquired by a second marking sensor which follows the first marking sensor. A second structure data record is thereby ascertained which represents the surface structure feature, wherein the defect position on the sheet material is identified by a comparison of the existing first structure data record with the second ascertained structure data record. If the structure data records match, a processing unit is actuated, which processes the sheet material in the region of the material defect, for example, by cutting out or repairing the material defect. The exact processing of the material defect could be chosen or selected according to the sheet material and/or material defect to be processed, and is not limited to removal or repair of the material defect.

The second marking sensor used corresponds in this situation to the first marking sensor, such that both marking sensors acquire the same surface structure feature. In this situation, too, the function of the marking sensors and the conversion parameters for converting the acquired surface structure features into the structure data record should be identical, in order to achieve good comparability.

The acquiring of the surface structure feature by the second marking sensor and the processing of the material defect can be carried out directly after the marking by the first marking sensor, such that, for example, a sheet material is marked and then conveyed onwards, and then, following this, the position of the material defect is acquired, identified, and processed.

It is also possible for the detection and processing of the material defect to be carried out at a later time, and, according to a further embodiment of the present application, for the sheet material to be rolled up, transported, and/or stored after the marking. It is therefore possible, for example, for a sheet material to be manufactured on a first apparatus, the material defect is acquired, and the sheet material is taken off the apparatus. It is then possible, on a further apparatus, for example one which is spatially separated, for example even after an intermediate further processing of the sheet material, for the detection and processing of the material defect to be carried out.

The comparison of the structure data records is, in most cases, carried out by a computer unit or a control unit. To what extent the structure data records must be or should be identical in order for concordance or agreement to be determined is to be specified individually by the user. It is possible, for example, for complete concordance or agreement to be specified as being identical, but it is also possible, for example, for concordance to be considered attained as soon as a concordance of the two structure data records is present above a certain tolerance threshold. When determining appropriate parameters, it is possible, for example, for a percentage figure value also to be determined, at which concordance will be deemed to have been reached. If the deviations between the data records are too great, however, there is the risk that, when the detection of the surface structure features starts again, sections will be identified as being concurrent which do not involve a section with a material defect.

In other words, the compared structure data records do not have to be identical to be considered to match or be in agreement. It is possible for a user to determine the minimum amount or degree to which the structure data records must match or correspond to one another in order to reasonably accurately determine the location of the material defect. For some users, it may be sufficient if a certain percentage of the two structure data records matches or corresponds or is identical. To further explain, in the technological area of criminal forensics, investigators might compare two images of a human fingerprint to determine if the two images are the same or correspond or are in agreement. Since it is highly unlikely that the two images will match exactly and be completely identical, the investigator analyzes the two images to see how many portions of the image match. If, for example, 90% or more of the lines and ridges that make up a human fingerprint are the same or match in each of the two images, it is possible that the investigator could reasonably conclude that it is highly likely that the two images have come from the fingerprint of a single person. If, for example, the percentage of matching is much lower, such as about 50% to 60%, the investigator may doubt that the two images were taken from the fingerprint of a single person. In much the same way, a user of a detection system, according to at least one possible embodiment of the present application, could determine a certain threshold that denotes a level of matching of the surface structures of the detected section or portion of the material that is sufficient to indicate that the section detected or marked by the second detection or marking sensor is the same section previously detected or marked by the first detection or marking sensor. The threshold or percentage of matching can be determined by the user based on preference. For some users, a higher percentage of matching in the range of about 80% to 100% may be desirable, whereas other users may find a lower percentage of matching, such as in the range of about 60% to 80% desirable. It should be understood that any range of matching in single percents or tenths of a percent can be selected by the user depending on the desired level of accuracy and precision.

After the detection of material defects, the sheet material frequently runs through various different apparatus elements, such as deflection rollers, guide devices, or processing units. In this situation, however, undesirable changes to the surface may occur, which, for example, also may affect the surface structure features which have been acquired. Thus, for example, friction, dirt contamination, or the like may occur, which can change surface structure features. In addition, one type of sheet material may have a different modulus of elasticity than another type of sheet material, and thus some sheet materials may stretch, sometimes substantially, more or less than others during handling or processing. Such elasticity may possibly be included or accounted for in the calculation or comparison processes. Further, some materials have higher or lower resilience, in that they can be more or less likely to return to their original shape or dimensions after deformation, such as by stretching or compression or shrinking. Some materials may experience a temporary deformation, whereas others may experience a more permanent deformation. These factors could also possibly be included or accounted for in the calculation or comparison processes.

In order to check and, if appropriate, determine whether constituent parts of an apparatus are changing or influencing the surface of the sheet material, provision is made according to a further embodiment of the present application that, between the first and the second marking sensor, at least one third marking sensor acquires the surface structure feature, and a third structure data record is ascertained. At least the first, second, and/or third structure data records are then compared with each other, and changes between the structure data records which correspond to changes in the surface structure features are ascertained. The determined changes are then taken into account, as appropriate, in the identification of the defect position.

By the arrangement of a third marking sensor, which corresponds to the first or second marking sensor, respectively, the location of the surface influence can be determined exactly or substantially exactly or generally. It is therefore possible, for example, for a third marking sensor to be positioned after the first marking sensor, before a deflection roller, and the second marking sensor behind the deflection roller. By way of the recording of the surface structure feature by the second and third marking sensor, and a comparison of the structure data derived from this, the influence of the deflection roller on the surface can be ascertained.

Such an arrangement can also be put into effect with a plurality of further marking sensors, which are arranged between the first and the second marking sensors.

If, for example, the changes in the surface structure features are of such a scale that they lead to an erroneous identification of the material defect, the changes which are ascertained can, for example, also be taken into account in the comparison of the structure data for the identification of the material defect.

In one possible embodiment of the present application, one improvement comprises the relative location and size of the position of the defect or the defect type and the location of the one or more surface structure features likewise being processed. This then means that downstream, after identification of the surface structure feature, the defect location or region can be determined directly.

According to a further embodiment of the present application, provision is made for an inlet sensor, between the first and the second marking sensor, to acquire the surface structure feature of the sheet material, before a second processing unit changes the surface structure of the sheet material, and produce (and store if appropriate) an input data record from the acquired surface structure features, which is compared with the first structure data record, and, if there is concordance between the first structure data record with the input data record, an outlet sensor acquires the surface structure feature from the sheet material emerging from the second processing station, taking account of the throughput speed of the sheet material through the two sensors and the distance interval of the sensors from one another, and an output data record is ascertained and stored.

This special embodiment allows for the use of the method in the event of the surface being processed in such a way that, on the basis of the first and second structure data records, an identification of the material defect would be impossible to achieve, or at least would be unreliable. Such processing steps can be, for example, the rolling or coating of the sheet material.

With the identification of the material defect at the inlet sensor, and taking into account the speed of the sheet material between the inlet sensor and the outlet sensor and the spacing interval of the two sensors from one another, the point of time is determined at which the sheet section with the material defect comes into the detection range of the outlet sensor. The outlet sensor then acquires the surface structure features—of the new surface—in the region of the material defect, and stores this as the output data record. In this way, despite a substantial change in the structure of the surface, the possibility of identifying the position of the material defect is still retained.

In other words, according to a further embodiment of the present application, an inlet sensor can be located or designed to operate between the first and the second marking sensor. The inlet sensor is designed to detect the surface structure feature of the sheet material before a second processing unit changes the surface structure of the sheet material. The inlet sensor then can produce and, if appropriate, store an input data record from the detected surface structure features. The input data record can then be compared with the first structure data record. If there is sufficient similarity between the first structure data record and the input data record, then the presence of the detected surface structure feature is verified. The section of sheet material containing the detected surface structure feature is then processed by the second processing unit. The second processing unit treats or processes or handles the sheet material in such a way that the surface structure of the sheet material is changed or altered to the point that the surface structure is substantially different from or no longer matches the surface structure as initially detected or recorded or marked by the first marking sensor. In such a situation, the data obtained by the second marking sensor regarding the surface structure would be insufficient to perform a comparison. The inlet sensor therefore essentially verifies the location or presence of the detected surface structure prior to the processing by the second processing unit. By taking into account the throughput speed of the sheet material, an outlet sensor detects the section of the sheet material that should contain the detected surface structure. In one possible embodiment, the inlet sensor is located essentially immediately upstream of the second processing station, and the outlet sensor essentially immediately downstream of the second processing station. Due to the proximity of the inlet and outlet sensors, a relatively reliable calculation can be made regarding when the detected surface structure, which has been altered by the second processing unit, is passing through or by the outlet sensor. When section of sheet material that is supposed to contain the detected surface structure passes by or through the outlet sensor, the outlet sensor detects and records and/or stores the altered or new surface structure as part of an output data record. This new data is then utilized to perform a comparison with the data obtained by the second marking sensor, much like is done when the sheet material is fed from the first marking sensor to the second marking sensor without a second processing unit disposed therebetween. If there is correspondence between the output data record and the data obtained by the second marking sensor, then the first processing unit for removing or repairing the defect is activated to remove or repair the defect or the section containing the defect. Such a method and system could be useful in a situation in which the sheet material is covered with a coating or altered by a treatment, such that the surface structure, as first detected, cannot or essentially cannot or substantially cannot be detected by the second marking sensor.

In one possible embodiment, the output data record produced from this and at least the first structure data record are compared, and the change ascertained, in order to check, for example, on the effectiveness of the second processing unit. This can be done, for example, by a check with existing reference values.

As an alternative or as a supplement, the output data record produced from this is used for the identification of the defect position on the sheet material, by a comparison of the present output data record instead of the first structure data record with the second structure data record ascertained.

The inlet sensor and the outlet sensor therefore correspond in their mode of function and effect to the marking sensors, or, respectively, they are marking sensors. The input and output data records are also ascertained in accordance with the structure data records, in order to achieve comparability with them.

In order to improve the precision of the identification or also to ensure or essentially ensure or promote a reliable detection of the surface structure features, for example, at very high sheet running speeds, such as in the paper industry, according to a further embodiment of the present application, a rough detection of the defect position is made, during which the defect position is ascertained by taking account of the sheet running speed.

In addition to this, in one possible embodiment, the detection of the surface structure features by the marking and/or input/outlet sensors (hereinafter marking sensors) can only take place or may take place as soon as, taking account of the rough detection, the entry of the surface structure ascertained by the first marking sensor into the detection range of the respective sensor is to be anticipated.

This means that it is possible, for example, for the surface structured data acquired by the marking sensors to be converted into structure data records when the sheet section with the material defect is acquired. As an alternative, the marking sensors may be activated as soon as the sheet section with the material defect comes into its detection range and/or it is possible for the data records or structure data records to be stored which comprise the defect area in the sheet material.

By way of the combination of the position determination with the identification, a perceptible easing of the burden on the apparatus used for the method is therefore achieved, in one possible embodiment for the sensors, memory unit, and, as appropriate, a control unit, which in turn leads to an economical performance of the method.

In order to ease the burden on the memory unit and to ensure or essentially ensure or promote reliable performance of the method, it is further possible for the data records stored in the memory unit to be deleted from the memory unit after the processing of the sheet section.

In principle it is possible for the marking sensors to acquire the sheet material permanently or substantially permanently and, respectively, also produce a permanent or substantially permanent structure data record. In this case, for the identification, the sections of the structure data records are used in which the surface structure feature is recognized. In at least one possible embodiment, a permanent or substantially permanent structure data record may include that the system recognizes when a relevant sheet section nears a sensor.

The expenditure for a permanent or substantially permanent detection is very high, however, since extremely high data quantities must be or should be processed. In this situation, the first and/or the second marking sensor acquires a surface structure feature, for one possible embodiment, from a section of the sheet material in which the material defect is present. Such a section, starting from the position of the material defect, exhibits, in one possible embodiment, a length of +/−one hundred fifty centimeters; in another possible embodiment, a length of +/−fifty centimeters; in yet a further embodiment, a length of +/−thirty centimeters; and/or in still a further embodiment, a length of +/−fifteen centimeters or less.

The section lengths according to the present application perceptibly increase the identification precision, since larger sheet section areas can be compared with one other. In one possible embodiment, in the event of unexpected surface changes, or even of surface changes which occur in only or some certain sections, which can be incurred, for example, by deflection rollers or also by dirt contamination, the comparison of larger sheet material sections may be effective. In other words, a larger detected section would provide many more surface structures or details to use in a comparison. As a result, even if some portion of the detected section were in some way altered during handling of the sheet material, there would still be much larger portions that would be unchanged or unaltered. These larger, unchanged portions would yield a sufficient number or amount of surface structures to perform a successful comparison of the data acquired by the marking sensors. Conversely, if the marking sensors only detect or acquire data regarding a smaller section of the sheet material, any alterations or changes may have a larger impact on the ability to make a successful comparison.

The sections acquired by the marking sensors can, in this situation, comprise both the sheet section at the position of the material defect as well as sheet sections before and/or after the position of the material defect. The length of the sheet sections may, for example, also be dependent on the speed of the sheet material, such that, with a web of paper, a longer section is acquired than with a strip of metal.

In principle, all or substantially all or some of the marking sensors present, input and outlet sensors, can be designed for the detection of the aforementioned sheet section areas.

The detection of the material defect can be carried out by means of conventional defect sensors, and is dependent in one possible embodiment on the type of material of which the sheet material comprises, and the surface properties which are to be acquired. According to a further embodiment of the present application, however, the material defect and/or the surface structure feature are acquired optically, wherein the material defect is, in one possible embodiment, acquired with an optical line scanning camera.

Optical detection systems can be used to particularly or substantially good effect with a moving sheet material, since they can be used very largely independently of the sheet running speed.

The detection of the surface structure feature can also be carried out by means of sensors, which, for example, carry out an optical detection. In this situation, for example, an image, in one possible embodiment a high-resolution image, is produced of the surface by means of a camera, from which the relevant surface structure features are read out.

According to a further embodiment of the present application, as surface structure features the roughness, transparency, color, and/or, in one possible embodiment, a scatter pattern of a laser light impinging on the surface of the sheet material, are acquired. The measuring of scatter patterns of a laser light is known by the expression Laser Surface Authentication Method (LSA). The LSA is in one possible embodiment well-suited, since scatter patterns of a laser light exhibit a particularly or relatively high degree of individuality. Added to this is the fact that the detection of scatter patterns is very largely independent of outside influences, such as, for example, light impingement.

As well as this, a camera system with polarization filter is suitable both as a defect sensor as well as a sensor for the detection of the surface structure feature (marking sensor, input/outlet sensor). This allows for the imaging of the surface in different polarization planes, as a result of which, for example, interfering light reflections on the surface of the sheet material can be filtered out during the ascertaining of the defects or the ascertaining of the surface structure feature. In one possible embodiment, a polarization camera is used, i.e. a camera which comprises an image sensor with a plurality of polarization filters, and is therefore in a position to acquire several polarization planes of light simultaneously or substantially simultaneously.

In principle, the method of the present application can be used with all or substantially all or most types of materials which are manufactured, used, or processed as sheet or strip materials. A precondition, however, is that the surface structure features can be acquired from the material while the sheet material is moving. The sheet material accordingly comprises in one possible embodiment a metal, a glass, a plastic, and/or of a substrate comprising cellulose, in one possible embodiment a paper or a board.

The present application further solves the object by an apparatus for the marking of a material defect in a sheet material, with a defect sensor for the detection of the material defect, with a moving sheet material, a first marking sensor which is designed such as to acquire a surface structure feature of the moving sheet material in the region of the material defect, and then store this as the first structure data record.

The apparatus of the present application therefore allows for a simple marking of a material defect in a sheet material, in that it brings the position of a material defect in the sheet material with a position of a surface structure feature into a dependency on one another. At the later re-finding of the material defect, therefore, there is no need and/or desire for a repeat material examination, which may under certain circumstances not be possible, nor for the elaborate finding of a characteristic feature which has been introduced. Rather, according to one possible embodiment, by means of a repeat detection of the surface structure features, it is relatively simple for the position of the material defect to be ascertained.

According to a further embodiment of the present application, the apparatus comprises, in addition to the features of the present application, at least: one second marking sensor, which is designed such as to acquire a surface structure feature of the sheet material, an apparatus for the production of a second of a second structure data record from the acquired surface structure features, an apparatus for the evaluation of data records, which is designed such as to compare at least the first and second structure data records, and an apparatus which, in the case of concordance of the structure data records, actuates a processing unit, which processes the sheet material in the region of the material defect.

The second marking sensor is designed such as to correspond to the first marking sensor, wherein the marking sensors are arranged in one possible embodiment also to produce the structure data record and to transfer this into a memory unit.

In addition or as an alternative, one or more control units can be provided, which, for example, produce the structure data records, evaluate and compare the data records, and/or actuate the processing unit.

For an exact or substantially exact or general identification, however, the measurement is made of a scatter pattern of a laser light impinging onto the surface of the sheet material. Accordingly, the first and second marking sensors are, for one possible embodiment, laser sensors, which acquire, as a surface structure feature, a scatter pattern of a laser light impinging onto the surface of the sheet material. Further marking sensors and/or input/outlet sensors can be designed accordingly.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

DESCRIPTION OF EMBODIMENT OR EMBODIMENTS

Figure 1:
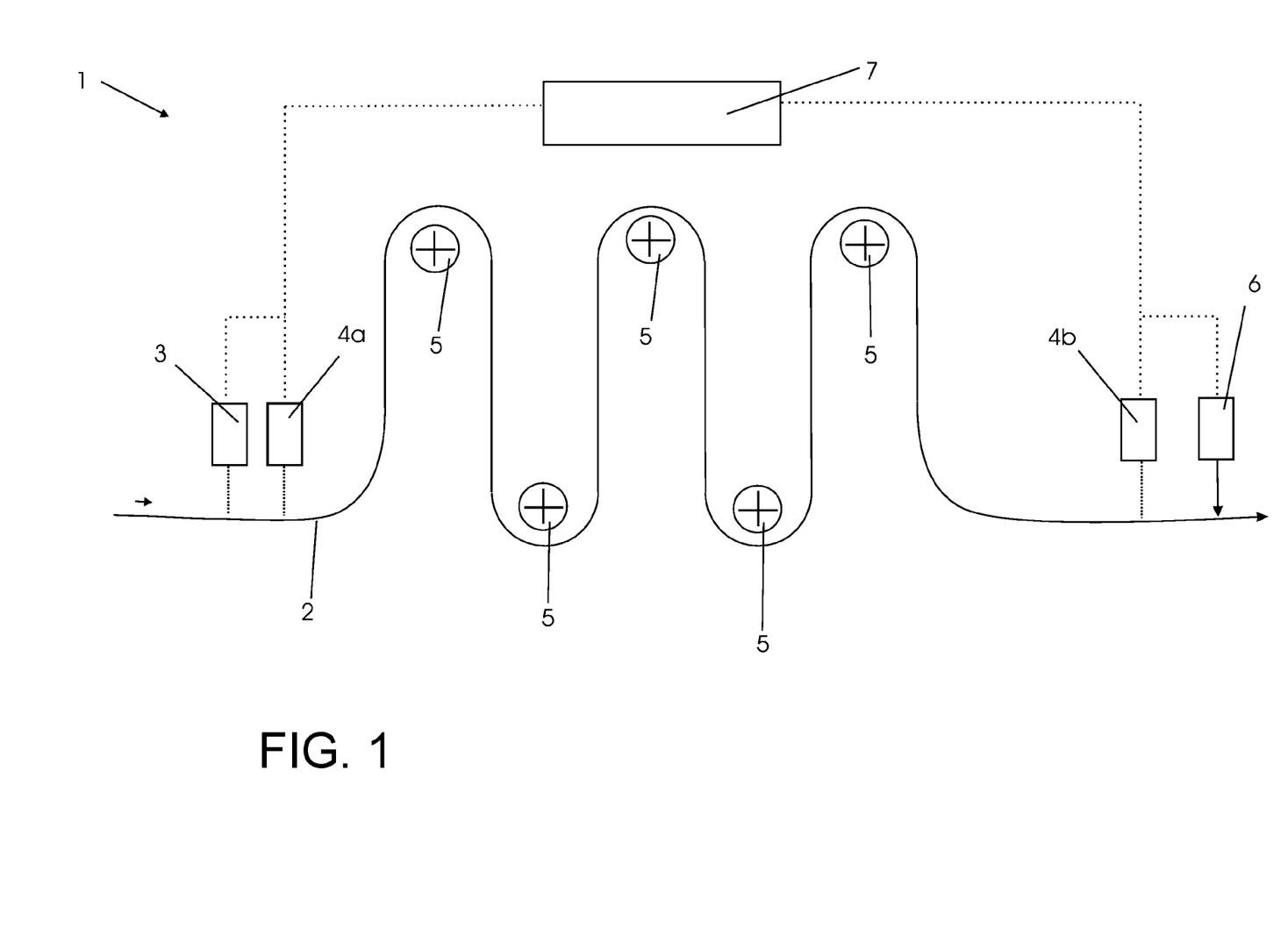
FIG. 1 shows in schematic form an apparatus for the marking, detection, and processing of a material defects in a sheet material.

FIG. 1 shows a sheet material 2, which is guided through an apparatus 1 for the marking, detection, and processing of a material defect in a sheet material. The sheet material 2 is a steel strip. The apparatus 1 further comprises an optical sensor 3, for example a line scanning camera, which is designed for the detection of defects, such as micro-cracks, in the surface of the sheet material 2.

Downstream of the optical sensor 3 in the direction of run of the strip is a first marking sensor 4a, which is a laser scatter light measuring device, designed in such a way as to carry out what is referred to as the LSA process.

The apparatus 1 further comprises a plurality of deflection rollers 5, around which the sheet material 2 is guided. For the detection of the position of the material defect, a second marking sensor 4b is put into arrangement, which is likewise designed as a laser scatter light measuring device.

Following in the direction of run of the sheet, arranged behind the second marking sensor 4b is a processing unit 6, which is designed as a steel strip cutting device.

The marking sensors 4a, 4b, the optical sensor 3 for the defect detection, and the first processing unit 6, are connected to one another via a control unit 7 (represented by broken lines).

In operation, the sheet material 2, coming from a roll (not shown here), is conducted past the optical sensor 3. The optical sensor 3 acquires the surface of the sheet material 2 and evaluates it. As soon as it detects a material defect, in this case a micro-crack, it sends a signal to the control unit 7.

The control unit 7 activates the first marking sensor 4a in such a way that it carries out a scatter light measurement on a section of the surface of the sheet material 2. In this situation the first marking sensor 4a acquires a surface section of the sheet material 2, located in which is the micro-crack ascertained by the optical sensor 3, i.e. the section acquired by the first marking sensor 4a is in a plane extending transversely to the direction of run of the sheet material 2, in which the micro-crack is also located.

In order to allow for better identification later, the marking sensor 4a acquires, in addition to the sheet section region in which the micro-crack was located, in each case a sheet section fifteen centimeters in front of and behind the region with the micro-crack; i.e., if the region with the micro-crack has a length of five centimeters in the direction of run of the strip, the sensor acquires a sheet section of a total of thirty-five centimeters long.

The surface structure features acquired by the marking sensor 4a, in this case the scatter of a laser light thrown by the marking sensor onto the sheet material surface, are converted into a structure data record, passed to the control unit 7, and stored there.

Further in operation, the sheet material 2 runs through the deflection rollers 5. As an alternative, for example, it would be possible for further processing units or guide devices to be arranged in this region.

At the end of the apparatus 1, the sheet material 2 enters into the detection region of the second marking sensor 4b. This acquires the same surface structure features as the first marking sensor 4a. The surface structure features which it has acquired are converted into a second structure data record and likewise transferred to the control unit 7. The control unit 7 compares the stored first structure data record with the second structure data record, and, if concordance is determined, then activates the processing unit 6, such that the sheet section with the micro-crack is separated out of the strip. In this case, the processing unit 6 separates out the complete region acquired of thirty-five centimeters. As an alternative, the control unit can also be designed such as to separate out short sheet sections, for example the micro-crack or the micro-crack with a short safety section.

Figure 2:
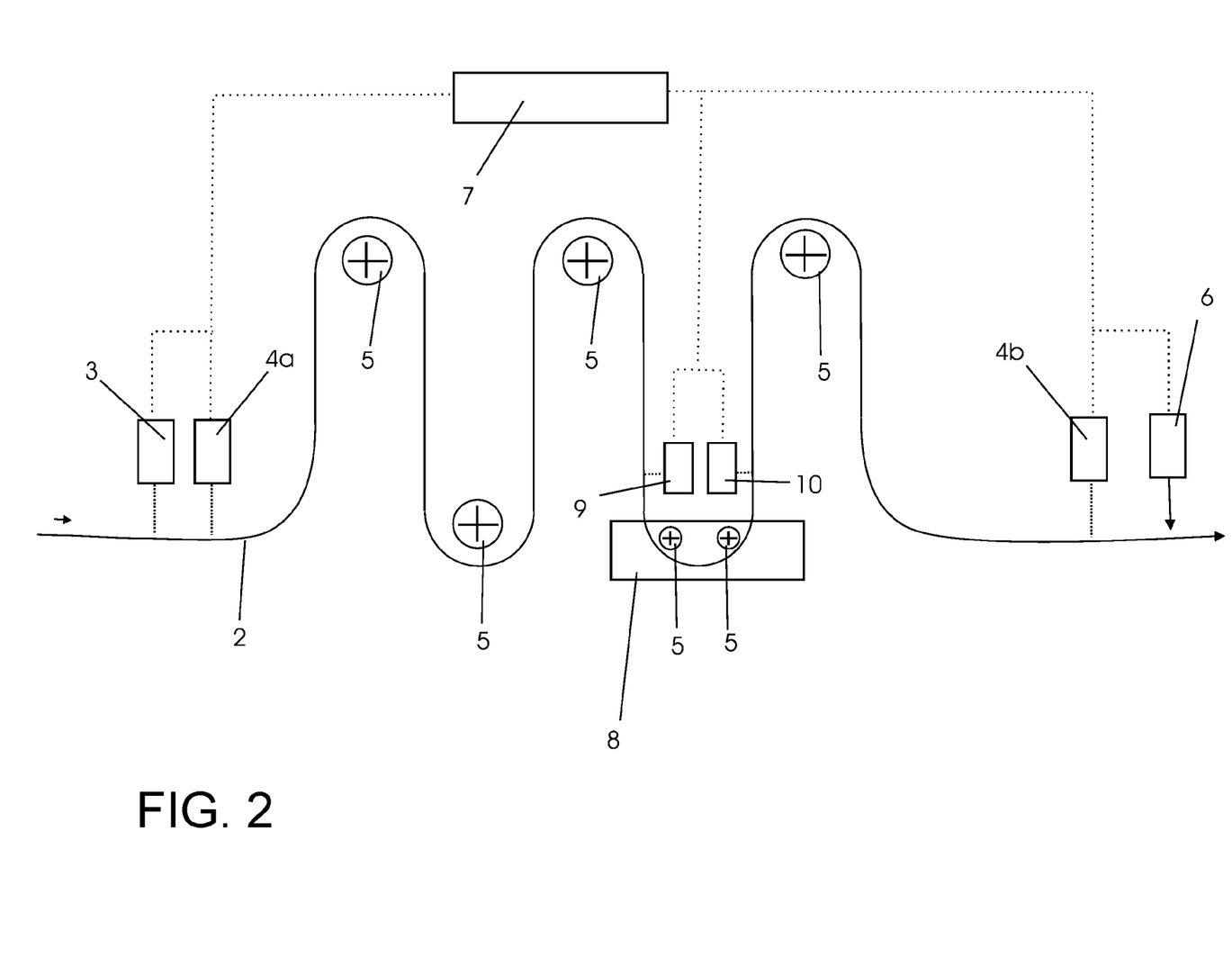
FIG. 2 shows in schematic form the apparatus from FIG. 1 with a second processing unit.

FIG. 2 shows, corresponding to FIG. 1, an apparatus 1 in schematic representation for the marking, detection, and processing of a material defect in a sheet material 2. In addition to the representation in FIG. 1, the sheet material 2 runs through a second processing unit 8, which in this case is designed as a galvanizing bath for the galvanizing of the surface of the steel strip. Because the surface galvanizing covers the surface structure features acquired by the marking sensor 4a, such that they cannot be found again by the second marking sensor 4b, an inlet sensor 9 is arranged before the entry into the second processing unit 8, and an outlet sensor 10 at the outlet of the second processing unit 8.

The inlet sensor 9 and the outlet sensor 10 are designed identical to the marking sensors 4a, 4b, which likewise carry out the LSA process. The surface structure features acquired by the inlet sensor 9 and the outlet sensor 10 are likewise transferred as input/output data records to the control unit 7. The control unit 7 in turn compares the data transferred by the inlet sensor 9 with the first structure data. As soon as there is a sufficient concordance or agreement of the two data records, the control unit 7 ascertains from the known sheet speed, and from the distance between the inlet sensor 9 and the outlet sensor 10, at what time the sheet section with the material defect enters the detection range of the outlet sensor 10.

With the time of the entry of the material defect into the detection range of the outlet sensor 10, this sensor ascertains the surface structure feature of the now galvanized surface of the sheet material 2 in the region of the material defect, converts this into an output data record, and transfers this to the control unit 7, which stores it.

For the identification of the material defect by the second marking sensor 4b, the control unit 7 now compares the structure data transferred from the second marking sensor 4b with the stored output data from the outlet sensor 10. Once sufficient concordance or agreement occurs, the control unit 7, in accordance with the representations in FIG. 1, activates the processing unit 6, which separates the defective sheet section out of the sheet material 2.

As an alternative, the control unit 7 is also designed, for example, to compare the inlet data record to be compared with the first structure data record, in order to determine what influence the deflection rollers 5, for example, exert on the surface. Accordingly, the control unit 7 can, for example, also compare the input data record with the output data record, by which the influence of the galvanizing bath can be ascertained. The output data record, or also the data relating to the change, can, for example, be compared with a reference value, in order to be able to determine whether the galvanizing bath was successful.

Likewise, as an alternative, further marking sensors can be provided for between the first and second marking sensors, for example in front of and behind a deflection roller 5, in order to ascertain the influence of a deflection roller 5 on the surface structure features. It would therefore be possible, for example, for individual apparatus elements (deflection roller, guide elements, etc.) which could cause interference to the sheet material, such as, for example, increased friction, wear, or dirt contamination to the surface, in a simple manner.

Although a number of aspects have been described in connection with the method, it is understood that these aspects also represent a description of the corresponding apparatus, such that, for example, a corresponding method step or a feature of a method step is also to be understood as an element of the apparatus. By analogy with this, aspects which have been described in connection with the apparatus also represent a description of a corresponding method step or a feature of a method step. In addition, the embodiments described herein above relate to the handling of a metal sheet material, though it should be understood that the principles of detecting and comparing data to permit the removal and/or repair of defects in the sheet material are equally applicable to all types of sheet material, such as plastic, paper, and glass.

The present application relates to a method for marking a material defect in a sheet material. In order to provide a method that can be used to identify a material defect in a sheet material particularly accurately or substantially accurately, reliably or substantially reliably, and permanently or substantially permanently, provision is made for a material defect in a moving sheet material to be sensed by a defect sensor and for a surface structure feature in the region of the sensed material defect to be sensed by a first marking sensor 4a and for a first structure data record representing the surface structure feature to be ascertained and stored.

One feature or aspect of an embodiment is believed at the time of the filing of this patent application to possibly reside broadly in a method for the marking of a material defect in a sheet material 2 comprising the steps: detection of a material defect in a moving sheet material 2 by a defect sensor 3, detection of at least one surface structure feature in the region of the acquired material defect by a first marking sensor 4a and preparation of a first structure data record representing the surface structure feature, and storing of the structure data record.

Another feature or aspect of an embodiment is believed at the time of the filing of this patent application to possibly reside broadly in the method for the marking, detection, and processing of a material defect in a sheet material 2, with the steps for marking the sheet material 2 according the present application, wherein, after the storing of the structure data record the surface structure feature is acquired by a second marking sensor 4b downstream of the first marking sensor 4a, and a second structure data record is created which represents the surface structure feature, the defect position on the sheet material 2 is identified by a comparison of the stored first structure data record with the second structure data record created, and in the case of concordance of the structure data records, a processing unit 6 is actuated, which processes the sheet material 2 in the region of the material defect.

Yet another feature or aspect of an embodiment is believed at the time of the filing of this patent application to possibly reside broadly in the method, wherein, after the detection of the surface structure feature, the sheet material is rolled up, transported, and/or stored.

Still another feature or aspect of an embodiment is believed at the time of the filing of this patent application to possibly reside broadly in the method, wherein, between the first and the second marking sensors 4a, 4b, at least one third marking sensor acquires the surface structure feature and a third structure data record is created, at least the first, second, and/or third structure data records are compared with each other, and changes between the structure data records which correspond to changes in the surface structure features are ascertained, and if appropriate, the changes which are ascertained are taken into account in the identification of the defect position.

A further feature or aspect of an embodiment is believed at the time of the filing of this patent application to possibly reside broadly in the method, wherein between the first and the second marking sensor 4a, 4b, an inlet sensor 9 acquires the surface structure feature of the sheet material 2, before a second processing unit 8 changes the surface structure of the sheet material 2, from the acquired surface structure feature an input data record is produced, and compared with the first structure data record, and in the case of concordance of the first structure data record with the input data record, an outlet sensor 10 acquires the surface structure feature of the sheet material 2 emerging from the second processing station, taking into account the runthrough speed of the sheet material 2 through the second processing unit 8, and an output data record is created and stored.

Another feature or aspect of an embodiment is believed at the time of the filing of this patent application to possibly reside broadly in the method, wherein the defect position on the sheet material 2 is identified by a comparison of the output data record present with the second structure data record ascertained, and/or the output data record and at least the first structure data record are compared and the change is acquired.

Yet another feature or aspect of an embodiment is believed at the time of the filing of this patent application to possibly reside broadly in the method, wherein a rough detection of the position of the material defect is carried out, taking into account a strip run speed, and/or the detection of the surface structure feature by the marking and/or input/outlet sensors 4a, 4b, 9, 10 takes place as soon as, taking account of the rough detection, the input of the surface structure ascertained by the first marking sensor 4a into the detection range of the respective sensor is available.

Still another feature or aspect of an embodiment is believed at the time of the filing of this patent application to possibly reside broadly in the method, wherein the stored structure data, input data, and/or output data is deleted from the storage or memory unit after the processing of the sheet section.

A further feature or aspect of an embodiment is believed at the time of the filing of this patent application to possibly reside broadly in the method, wherein the first and/or the second marking sensor 4a, 4b acquires a surface structure feature from a section of the sheet material 2 in which the material defect is present, wherein the section, starting from the position of the material defect, exhibits in one possible embodiment a length of +/−seventy-five centimeters, in another possible embodiment +/−fifty, in yet another possible embodiment +/−thirty centimeters, and/or in still another possible embodiment +/−fifteen centimeters or less.

Another feature or aspect of an embodiment is believed at the time of the filing of this patent application to possibly reside broadly in the method, wherein the material defect and/or the surface structure feature is optically acquired, wherein the material defect is in one possible embodiment acquired by an optical line scanning camera.

Yet another feature or aspect of an embodiment is believed at the time of the filing of this patent application to possibly reside broadly in the method, wherein, as surface structure features, the roughness, transparency, color, and/or, in one possible embodiment, a scatter pattern of a laser light impinging onto the surface of the sheet material 2 is acquired.

Still another feature or aspect of an embodiment is believed at the time of the filing of this patent application to possibly reside broadly in the method, wherein the sheet material 2 comprises a metal, a glass, a plastic, and/or a substrate comprising cellulose, in one possible embodiment a paper or a board.

One feature or aspect of an embodiment is believed at the time of the filing of this patent application to possibly reside broadly in an apparatus for the marking of a material defect in a sheet material 2, with a defect sensor for the detection of the material defect with a moving sheet material 2, a first marking sensor 4a, which is designed to acquire a surface structure feature of the moving sheet material 2 in the region of the material defect, from this, to create a first structure data record, and to store this in a memory unit.

Another feature or aspect of an embodiment is believed at the time of the filing of this patent application to possibly reside broadly in the apparatus for the marking, finding, and processing of a material defect in a sheet material 2, with an apparatus according to the present application and with a second marking sensor 4b, which is designed to acquire a surface structure feature of the sheet material 2, an apparatus for the creation of a second structure data record from surface structure features acquired, an apparatus for the evaluation of data records, which is designed to compare at least the first and second structure data records, and an apparatus which, at the concordance of the structure data records, actuates a processing unit which processes the sheet material 2 in the region of the material defect.

Yet another feature or aspect of an embodiment is believed at the time of the filing of this patent application to possibly reside broadly in the apparatus, wherein the first, second, and/or at least one further marking sensor 4a, 4b is a laser sensor, which, as a surface structure feature, acquires a scatter pattern of a laser light impinging onto the surface of the sheet material 2.

The components disclosed in the patents, patent applications, patent publications, and other documents disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications, patent publications, and other documents cited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, patent applications, patent publications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, patent applications, patent publications, and other documents either incorporated by reference or not incorporated by reference.

All of the patents, patent applications, patent publications, and other documents, except for the exceptions indicated herein, which were cited in the International Search Report having a mailing date of Nov. 17, 2014, and/or cited elsewhere, as well as the International Search Report document itself, are hereby incorporated by reference as if set forth in their entirety herein except for the exceptions indicated herein, as follows: U.S. Patent Publication No. 2010/063750 A1; German Patent Publication No. 10 2009 029084 A1; and U.S. Patent Publication No. 2012/057162 A1.

All of the patents, patent applications, patent publications, and other documents, except for the exceptions indicated herein, which were cited in the German Office Action dated Mar. 24, 2014, and/or cited elsewhere, as well as the German Office Action document itself, are hereby incorporated by reference as if set forth in their entirety herein except for the exceptions indicated herein, as follows: DE 10 2004 010 479 A1.

The corresponding foreign and international patent publication applications, namely, Federal Republic of Germany Patent Application No. 10 2013 108 485.0, filed on Aug. 6, 2013, having inventors Jürgen-Peter HERRMANN, Marius Michael HERRMANN, and Wolfgang SCHORN, and DE-OS 10 2013 108 485.0 and DE-PS 10 2013 108 485.0, and International Application No. PCT/EP2014/066630, filed on Aug. 1, 2014, having WIPO Publication No. WO 2015/018759 A1 and inventors Jürgen-Peter HERRMANN, Marius Michael HERRMANN, and Wolfgang SCHORN, are hereby incorporated by reference as if set forth in their entirety herein, except for the exceptions indicated herein, for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications, patent publications, and other documents, except for the exceptions indicated herein, are hereby incorporated by reference as if set forth in their entirety herein except for the exceptions indicated herein.

The purpose of incorporating the corresponding foreign equivalent patent application(s), that is, PCT/EP2014/066630 and German Patent Application 10 2013 108 485.0, is solely for the purposes of providing a basis of correction of any wording in the pages of the present application, which may have been mistranslated or misinterpreted by the translator, and to provide additional information relating to technical features of one or more embodiments, which information may not be completely disclosed in the wording in the pages of this application.

Statements made in the original foreign patent applications PCT/EP2014/066630 and DE 10 2013 108 485.0 from which this patent application claims priority which do not have to do with the correction of the translation in this patent application are not to be included in this patent application in the incorporation by reference.

Any statements about admissions of prior art in the original foreign patent applications PCT/EP2014/066630 and DE 10 2013 108 485.0 are not to be included in this patent application in the incorporation by reference, since the laws relating to prior art in non-U.S. Patent Offices and courts may be substantially different from the Patent Laws of the United States.

The following U.S. patents and patent application publications, except for the exceptions indicated herein, are hereby incorporated by reference as if set forth in their entirety herein except for the exceptions indicated herein, as follows: U.S. Patent Application Publication No. 2007/0165208; U.S. Patent Application Publication No. 2010/316251; U.S. Pat. Nos. 9,220,446; 8,867,134; 8,786,839; and 8,755,121.

The following U.S. patents and patent application publications, foreign patents and patent application publications, non-patent literature, and other documents, except for the exceptions indicated herein, are hereby incorporated by reference as if set forth in their entirety herein except for the exceptions indicated herein, as follows: U.S. Patent Application No. 2009/0283583, having the title "TWO TIER AUTHENTICATION", published on Nov. 19, 2009; European Patent Application No. 2 110 776 A2, having the title "Optical authentication", published on Oct. 21, 2009; Great Britain Patent No. 919,664, having the title "BALLSCREW AND NUT TRANSMISSION ASSEMBLY", published on Feb. 27, 1963; "Laser Surface Authentication™: Natural Randomness as a Fingerprint for Product Authentication and Tracking", © Ingenia Technology (UK) Ltd, 2010; "Laser Surface Authentication™: Natural Randomness as a Fingerprint for Product Authentication" by Mark McGlade, Director Business Development, Ingenia Technology Ltd., © Ingenia Technology (UK) Ltd, 2006; "Laser-Streulichtmessungen zur Verpackungsidentifizierung und-verfolgung: Einsatzmöglichkeiten in der Prozessindustrie" by Ludger Brüll and Martin Friedrich, Bayer Technology Services GmbH, 2007; and "PROTEXXION Powered by LSA: Die neue Dimension der Fälschungssicherheit: Eindeutige Authentifizierung ohne Markierung", © Bayer Technology Services, 2007.

All of the references and documents cited in any of the patents, patent applications, patent publications, and other documents cited herein, except for the exceptions indicated herein, are hereby incorporated by reference as if set forth in their entirety herein except for the exceptions indicated herein. All of the patents, patent applications, patent publications, and other documents cited herein, referred to in the immediately preceding sentence, include all of the patents, patent applications, patent publications, and other documents cited anywhere in the present application.

Words relating to the opinions and judgments of the author of all patents, patent applications, patent publications, and other documents cited herein and not directly relating to the technical details of the description of the embodiments therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, patent publications, and other documents, are not considered to be incorporated by reference herein for any of the patents, patent applications, patent publications, and other documents cited herein.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications, patent publications, and other documents cited herein may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. § 1.72(b). As stated in 37 C.F.R. § 1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A method of using a tracking arrangement for the tracking of a material defect in a sheet material comprising a container material or a product-packaging material, said method comprising the steps of:

moving a sheet material through or past a defect sensor configured to detect a material defect in a sheet material moving thereby or therethrough, and then detecting, with said defect sensor, a material defect in said sheet material;

detecting, with a first structure sensor configured to detect at least one inherent structural feature of the sheet material itself in the region of the material defect, at least one inherent structural feature of said sheet material itself in the region of said material defect, which said at least one inherent structural feature being usable as a reference for determining the position of said material defect in said sheet material; and receiving data from said first structure sensor with a control arrangement, and thereby preparing and storing a first structure data record representing said at least one inherent structural feature as detected by said first structure sensor.

2. The method according to claim 1, wherein said tracking arrangement further comprises a second structure sensor disposed downstream of said first structure sensor, and configured to detect inherent structural features of the sheet material; said tracking arrangement further comprises a processing unit configured to process a portion of the sheet material containing the material defect; and said method further comprises:
    moving said sheet material to said second structure sensor after detection of said at least one inherent structural feature by said first structure sensor;
    moving said sheet material through or past said second structure sensor, and then detecting, with said second structure sensor, inherent structural features of said sheet material;
    receiving data, with said control arrangement, from said second structure sensor, and thereby preparing and storing a second structure data record representing the inherent structural features as detected by said second structure sensor;
    comparing, with said control arrangement, the second structure data record with the first structure data record, and thus comparing the inherent structural features detected by said second structure sensor with said at least one inherent structural feature detected by said first structure sensor; and
    upon determining that an inherent structural feature detected by said second structure sensor matches sufficiently with said at least one inherent structural feature detected by said first structure sensor, and thus detecting that said material defect is in a position to be processed, actuating, with said control arrangement, a processing unit and processing the portion of said sheet material containing said material defect.

3. The method according to claim 2, wherein said step of moving said sheet material after the detection of said at least one inherent structural feature comprises one of:
    moving said sheet material in a single handling arrangement comprising both said first structure sensor and said second structure sensor; or
    removing said sheet material from a first handling arrangement comprising said first structure sensor and then moving said sheet material to a second, separate, handling arrangement comprising said second structure sensor, wherein said sheet material is rolled up, transported, and/or stored before being moved to said second, separate, handling arrangement.

4. The method according to claim 3, wherein:
    between said first structure sensor and said second structure sensor, at least one third structure sensor detects said at least one inherent structural feature and a third structure data record is created;
    at least said first, second, and/or third structure data records are compared with each other; and
    changes between said structure data records which correspond to changes in said at least one inherent structural features are ascertained, and if appropriate, the changes which are ascertained are taken into account in the identification of the defect position.

5. The method according to claim 4, wherein:
    between said first structure sensor and said second structure sensor, an inlet sensor acquires said at least one inherent structural feature of said sheet material before a second processing unit changes or alters said at least one inherent structural feature of said sheet material;
    from said acquired inherent structural feature an input data record is produced, and compared with said first structure data record; and
    in the case of concordance of said first structure data record with said input data record, an outlet sensor acquires said at least one inherent structural feature of said sheet material emerging from said second processing station, taking into account the runthrough speed of said sheet material through said second processing unit; and
    an output data record is created and stored.

6. The method according to claim 5, wherein:
    the position of said material defect on said sheet material is identified by a comparison of said output data record present with said second structure data record ascertained, and/or
    said output data record and at least said first structure data record are compared and the change is acquired.

7. The method according to claim 6, wherein:
    a rough detection of the position of said material defect is carried out, taking into account a strip run speed; and/or
    detection of said at least one inherent structural feature by said structure sensors and/or said input/outlet sensors takes place as soon as, taking account of the rough detection, the input of said surface structure ascertained by said first structure sensor into the detection range of the respective sensor is available.

8. The method according to claim 7, wherein said stored structure data, input data, and/or output data is deleted from said storage or memory unit after the processing of said sheet section.

9. The method according to claim 8, wherein said first structure sensor and/or said second structure sensor acquires said at least one inherent structural feature from a section of said sheet material in which said material defect is present, wherein said section, starting from the position of said material defect, exhibits in particular a length of one of: +/−75 centimeters, +/−50 centimeters, +/−30 centimeters, or +/−15 centimeters or less.

10. The method according to claim 9, wherein said material defect and/or said at least one inherent structural feature is optically acquired, or said material defect is acquired by an optical line scanning camera.

11. The method according to claim 10, wherein as inherent structural features, the roughness, transparency, color, and/or a scatter pattern of a laser light impinging onto the surface of said sheet material is acquired.

12. The method according to claim 11, wherein said sheet material comprises a metal, a glass, a plastic, and/or a substrate containing cellulose, paper or paperboard.

13. The method according to claim 2, wherein:
    between said first structure sensor and said second structure sensor, at least one third structure sensor detects said at least one inherent structural feature and a third structure data record is created;
    at least said first, second, and/or third structure data records are compared with each other; and
    changes between said structure data records which correspond to changes in said at least one inherent structural features are ascertained, and if appropriate, the changes which are ascertained are taken into account in the identification of the defect position.

14. The method according to claim 2, wherein:
    between said first structure sensor and said second structure sensor, an inlet sensor acquires said at least one inherent structural feature of said sheet material before a second processing unit changes or alters said at least one inherent structural feature of said sheet material;
    from said acquired inherent structural feature an input data record is produced, and compared with said first structure data record; and
    in the case of concordance of said first structure data record with said input data record, an outlet sensor acquires said at least one inherent structural feature of said sheet material emerging from said second processing station, taking into account the runthrough speed of said sheet material through said second processing unit; and an output data record is created and stored;

the position of said material defect on said sheet material is identified by a comparison of said output data record present with said second structure data record ascertained, and/or said output data record and at least said first structure data record are compared and the change is acquired.

15. The method according to claim 2, wherein:
a rough detection of the position of said material defect is carried out, taking into account a strip run speed; and/or
detection of said at least one inherent structural feature by said structure sensors and/or said input/outlet sensors takes place as soon as, taking account of the rough detection, the input of said surface structure ascertained by said first structure sensor into the detection range of the respective sensor is available.

16. The method according to claim 2, wherein at least one of (A) and (B):
   (A) said stored structure data, input data, and/or output data is deleted from said storage or memory unit after the processing of said sheet section; and
   (B) said first structure sensor and/or said second structure sensor acquires said at least one inherent structural feature from a section of said sheet material in which said material defect is present, wherein said section, starting from the position of said material defect, exhibits in particular a length of one of: +/−75 centimeters, +/−50 centimeters, +/−30 centimeters, or +/−15 centimeters or less.

17. The method according to claim 2, wherein at least one of (C), (D), and (E):
   (C) said material defect and/or said at least one inherent structural feature is optically acquired, or said material defect is acquired by an optical line scanning camera;
   (D) as inherent structural features, the roughness, transparency, color, and/or a scatter pattern of a laser light impinging onto the surface of said sheet material is acquired; and
   (E) said sheet material comprises a metal, a glass, a plastic, and/or a substrate containing cellulose, paper or paperboard.

18. The method according to claim 2, wherein at least one of said first and second structure sensors is a laser sensor configured to acquire a scatter pattern of a laser light, and said method further comprises impinging with laser light onto the surface of the sheet material at the at least one surface structure, and then acquiring, with said laser sensor, a scatter pattern of the laser light.

19. The method according to claim 3, wherein at least one of said first and second structure sensors is a laser sensor configured to acquire a scatter pattern of a laser light, and said method further comprises impinging with laser light onto the surface of the sheet material at the at least one surface structure, and then acquiring, with said laser sensor, a scatter pattern of the laser light.

20. The method according to claim 4, wherein at least one of said first, second, and third structure sensors is a laser sensor configured to acquire a scatter pattern of a laser light, and said method further comprises impinging with laser light onto the surface of the sheet material at the at least one surface structure, and then acquiring, with said laser sensor, a scatter pattern of the laser light.

* * * * *